United States Patent [19]
Hool

[11] Patent Number: 5,218,841
[45] Date of Patent: Jun. 15, 1993

[54] APPARATUS AND METHODS FOR DETERMINING LIQUID/LIQUID INTERFACIAL TENSION AND DYNAMIC INTERFACIAL TENSION REDUCTION

[75] Inventor: Kevin O. Hool, Midland, Mich.

[73] Assignee: The Dow Chemical Company, Midland, Mich.

[21] Appl. No.: 931,887

[22] Filed: Aug. 18, 1992

Related U.S. Application Data

[63] Continuation of Ser. No. 610,197, Nov. 5, 1990, abandoned.

[51] Int. Cl.$^5$ .......................................... G01N 13/02
[52] U.S. Cl. ............................................... 73/64.52
[58] Field of Search ..................................... 73/64.52

[56] References Cited

U.S. PATENT DOCUMENTS

| | | | |
|---|---|---|---|
| 3,913,385 | 10/1975 | Jobe | 73/64.4 |
| 4,196,615 | 4/1980 | Davis | 73/64.4 |
| 4,391,129 | 7/1983 | Trinh et al. | 73/64.4 |
| 4,697,451 | 10/1987 | Matteson | 73/64.4 |

FOREIGN PATENT DOCUMENTS

| | | | |
|---|---|---|---|
| 2436599 | 2/1976 | Fed. Rep. of Germany | 73/64.4 |
| 0024670 | 2/1980 | Japan | 73/64.4 |

OTHER PUBLICATIONS

IBM Technical Bulletin vol. 22 No. 5 (Oct. 1979) pp. 2082-2083 Titcomb, S. C. "Instrument for Measuring Dynamic Surface Tension".

Journal of Colloid and Interface Science vol. 60 No. 1 (Jun. 1, 1977) pp. 50-53 Tornberg, Eva "A Surface Tension Apparatus According to the Drop Volume Principle".

Brochure by Lauda regarding Tropfenvolumen-Tensiometer TVT 1 (Translation of Three Paragraphs marked by an Asterisk) (May 1988).

Brochure by Brinkmann, regarding Lauda Tensiometers for Science Quality Surface Measurements (Aug. 1987).

Primary Examiner—Herbert Goldstein
Assistant Examiner—Raymond Y. Mah

[57] ABSTRACT

Apparatus and methods for determining the liquid/liquid interfacial tension between immiscible liquids wherein a first liquid is introduced into a second liquid at a constant rate of flow sufficient to produce successive, uniform size drops which ascend or descend depending upon whether the first liquid has a lower or higher density than that of the second liquid. The apparatus and methods are particularly useful in evaluating the effectiveness of a surfactant and the dynamics of interfacial reduction. In practice, the first liquid is discharged into the second liquid through a nozzle having an outlet of very low surface area. The time required to produce a selected number of drops is inversely proportional to the ability of the surfactant to reduce interfacial tension between the two liquids.

36 Claims, 2 Drawing Sheets

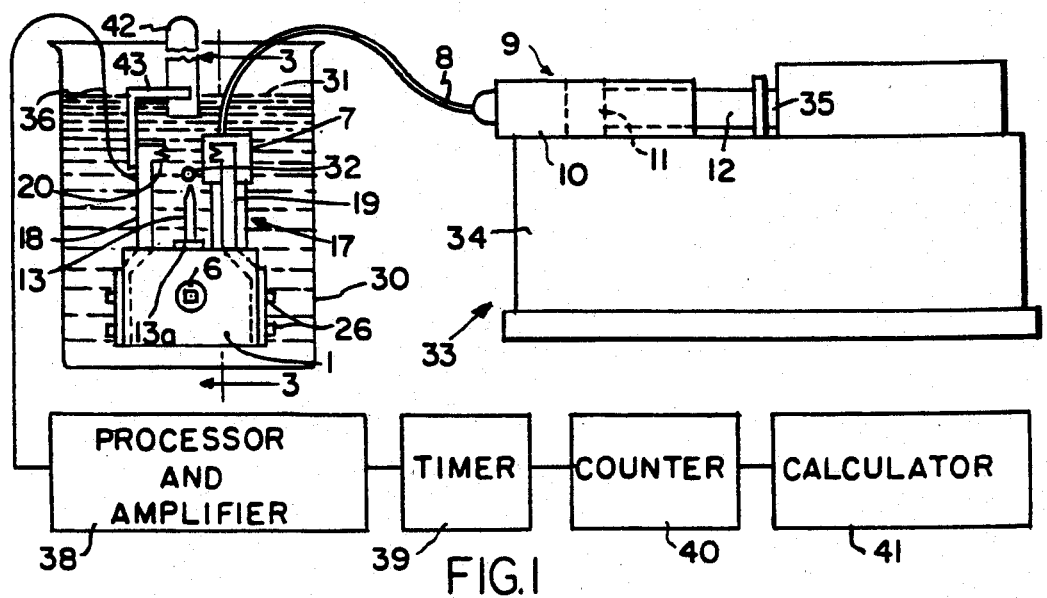
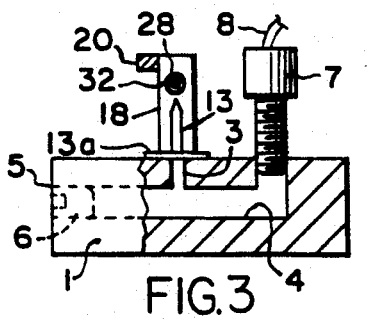
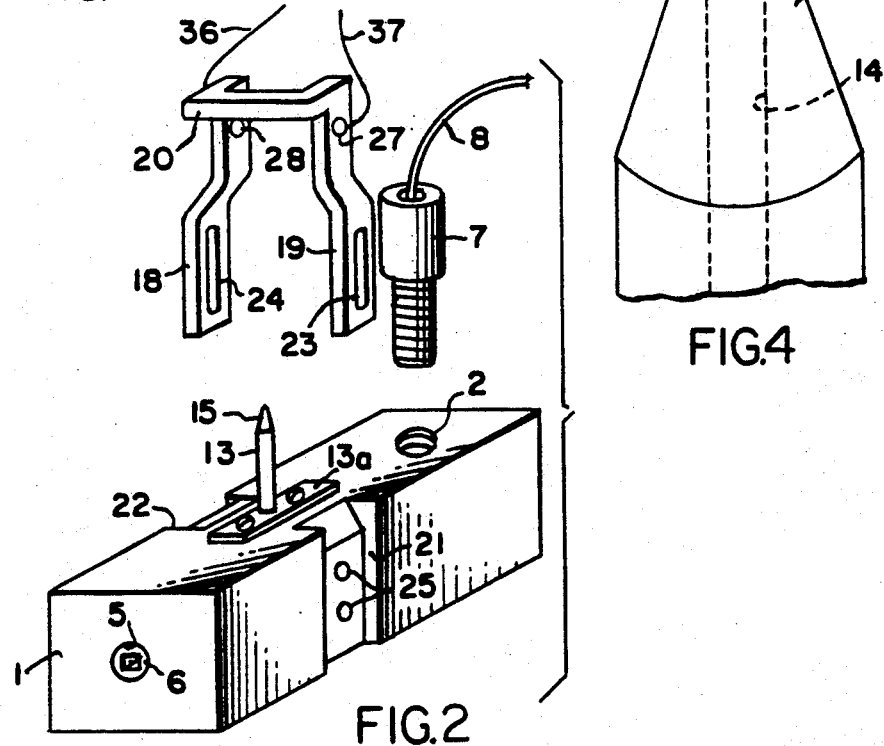

APPARATUS AND METHODS FOR DETERMINING LIQUID/LIQUID INTERFACIAL TENSION AND DYNAMIC INTERFACIAL TENSION REDUCTION

CROSS-REFERENCE TO RELATED APPLICATION

This is a continuation of application Ser. No. 07/610,197, filed Nov. 6, 1990, now abandoned.

This invention relates to apparatus and methods for determining liquid/liquid interfacial tension and evaluating the dynamics of interfacial tension reduction, such apparatus and methods being especially applicable for use in ascertaining the effectiveness of surfactants in reducing interfacial tension between immiscible liquids.

BACKGROUND OF THE INVENTION

Several techniques presently exist for measuring liquid/liquid interfacial tension for the purpose of predicting surfactant performance. Among them are the spinning drop method, the shear field method, the electric field method, the duNouy ring method, the sessile/pendant drop method, and the drop weight method.

Of the methods referred to above the drop weight method is the most similar to the methods disclosed herein, but the methods according to the invention are considerably simpler and more effective for their purpose than is the drop weight method.

In the drop weight method of measuring interfacial tension the weight of each drop is measured in a laborious manner: after each liquid drop has formed and detached, the reservoir of liquid being dispersed by the surfactant is manually weighed. The difference in weight before and after the drop detachment is assumed to be the drop weight. This approach is labor intensive and subject to high probability of producing erroneous data due to human intervention and manipulation.

The drop weight method relies upon Tate's Law extended by the Scheele and Meister development work and modified by Harkin's correction factor due to the necessity of accounting for the fluid volume remaining attached to the dispensing fluid orifice after detachment of each liquid drop. Tate's Law, as modified by Sheele and Meister, is applicable only in those cases in which no surfactant is present in the liquid into which the drop is dispensed and the Harkin's correction is applied to account for liquid left at the dispensing orifice following detachment of a drop.

None of the known methods referred to above for measuring liquid/liquid interfacial tension provides any information with respect to the dynamic aspects of interfacial tension reduction of a liquid/liquid interface by a surfactant. In the methods disclosed herein, however, a measure of the dynamic aspects of such interfacial tension reduction is obtainable.

Among the objects of the present invention is to simplify the measurement of liquid/liquid interfacial tension primarily for the purpose of evaluating the effectiveness of surfactants on various immiscible liquids.

Another object of the invention is to provide a method for the evaluation of the dynamic characteristics of interfacial tension reduction due to the presence of surfactants.

SUMMARY OF THE INVENTION

The interfacial tension between immiscible liquids can be measured according to the invention by forming and counting drops of one liquid detached from a dispensing nozzle submerged in another liquid, the tip of such nozzle having a geometry which avoids a varying wetting profile thereby enabling each successive drop to be a virtually uniform size. It thus is possible to determine accurately the liquid/liquid interfacial tension simply by counting the drops and without having to use the Harkin or other correction factor. The invention thus is particularly adapted for predicting the effectiveness of a surfactant in reducing the liquid/liquid interfacial tension.

The invention provides for the dispensing of a first drop-forming liquid into a second, immiscible liquid at a uniform flow rate sufficient to enable drops of the first liquid to be formed in the second liquid. Either or both of the liquids may contain a surfactant which reduces interfacial tension between the drop and the liquid into which the drop is introduced.

The drop-forming phase or liquid is dispensed through a tube having a nozzle that is immersed in a second liquid contained in a vessel, such second liquid hereinafter sometimes being referred to as a continuous phase. The surface area of the nozzle tip which surrounds the dispensing nozzle is made as close to a razor edge as possible, consistent with machining limitations to avoid irregularities, so as to expose as little area as possible to wetting by the contents of the vessel, thereby providing a constant circumference of the attachment of the drop to the nozzle tip regardless of the liquids used.

If the liquid phase from which the drops are formed is of lower density than that of the liquid of the continuous phase into which the drops are dispensed, the drops will rise. If the drop-forming liquid phase is of greater density than that of the continuous phase into which the drops are dispensed, the drops will descend. In either case, the number of drops produced may be counted.

The dispensing of the drop-forming liquid into the continuous phase is effected at such a rate of flow as to avoid any appreciable contribution to drop detachment due to momentum. As a consequence, the detachment of each drop from the nozzle will be due primarily to the force balance between the adherence force (defined as the product of the interfacial tension times the circumference of the nozzle tip) and a separation force (defined as the product of the drop volume times the difference in densities between the two liquids and the gravity constant).

THE DRAWINGS

Apparatus for practicing the invention is disclosed in the accompanying drawings, wherein:

FIG. 1 is a side elevational and diagrammatic view of the apparatus;

FIG. 2 is a fragmentary, enlarged, exploded view of some of the components of the apparatus shown in FIG. 1;

FIG. 3 is a sectional view taken on the line 3—3 of FIG. 1;

FIG. 4 is a fragmentary, greatly enlarged isometric view, partly in section, of a nozzle forming part of the invention.

THE DISCLOSED EMBODIMENTS

Figure 5:
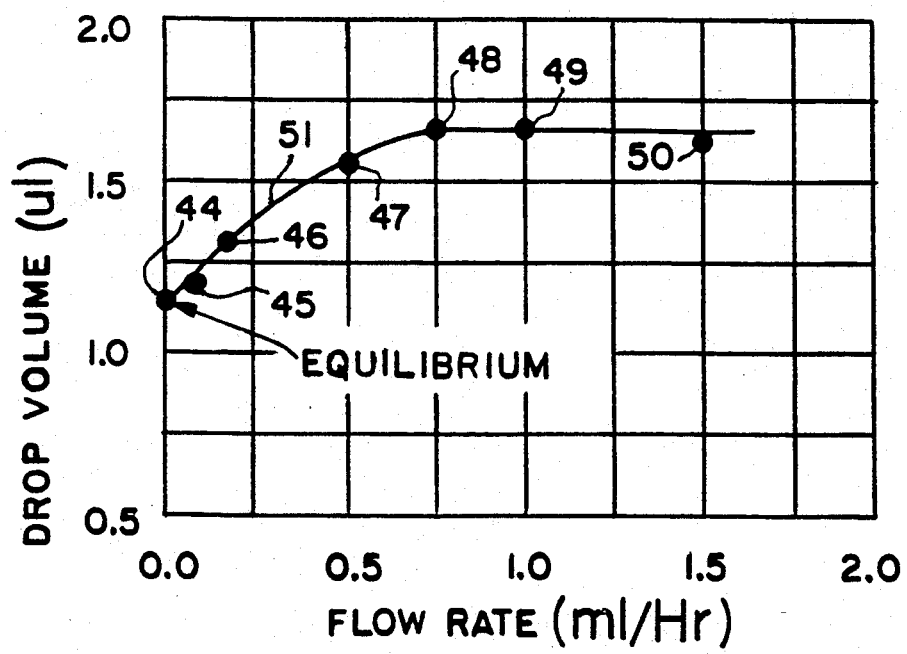
FIG. 5 is a diagram illustrating the dynamic effects of interfacial tension reduction as a result of varying the rate of flow of the dispensed liquid.

Apparatus constructed in accordance with a preferred embodiment of the invention comprises a manifold block 1 having an inlet port 2, an outlet port 3, a passage 4 connecting the inlet and outlet ports, and an access port 5 that normally is closed by a threaded plug 6. All of the parts are formed from materials which are compatible with each other and inert to the liquids being used.

Fitted into the inlet port 2 is an inlet nipple 7 to which is coupled one end of a liquid delivery tube 8, the opposite end of which is coupled to a syringe 9 having a barrel 10 within which is accommodated a supply of a drop forming liquid and a reciprocable piston 11 fixed to an operating stem 12.

A tubular discharge member 13, formed preferably of tungsten carbide, is separably secured at one end to the block 1 by means of a mounting plate 13a and gasket (not shown). The member 13 has a bore 14 in communication with the passage 4. The member 13 terminates at its free end in a frustoconical nozzle 15. As is best shown in FIG. 4 the free end of the nozzle terminates in an annular, convex tip 16 the radial thickness of which is substantially less than the radial thickness of any other portion of the wall of the member 13 or the nozzle 15. The area of the surface 16 is exaggerated in FIG. 4. The surface of the tip 16 ideally is a razor edge for the purpose of defining a constant circumference of the nozzle outlet, but machining limitations cause the surface to be of finite area.

A sensor supporting frame 17 comprises a pair of parallel legs 18 and 19 joined at their upper ends by a laterally offset cross bar 20. The legs 18 and 19 straddle the manifold block 1 and are accommodated in guides 21 and 22, respectively, formed on opposite sides of the discharge member 13. The legs are provided with slots 23 and 24 for the accommodation of bolts 26 which may be threaded into openings 25 formed in the block 1 to enable the frame 17 to be supported at a selected level.

Adjacent their upper ends the legs 18 and 19 are apertured for the accommodation of optical sensing means comprising a light emitting diode 27 and a photodiode receiver 28. The light emitting diode is arranged to transmit a beam along a horizontal path toward the photodiode 28. To shorten the path length between the diodes 27 and 28 the upper ends of the legs 18 and 19 are bent toward each other as is best shown in FIG. 2.

The assembly of the manifold block 1, the frame 17, and their associated parts is adapted to be placed within a vessel 30 containing a continuous phase or first liquid 31 having a depth sufficient that its surface extends to a level above the upper part of the frame 17. The syringe 9 contains a second, drop-forming liquid that is immiscible with the liquid 31. Displacement of the piston 11 inwardly of the barrel 10 will cause liquid to be delivered from the syringe through the nozzle 15 via the line 8, the inlet fitting 7, the passages 3 and 4, and the bore 14 of the member 13.

The flow rate at which the liquid from the syringe is delivered through the nozzle tip 16 should be such that the discharged liquid forms successive drops 32, rather than a stream. Preferably, the flow rate is in a range the upper value of which is such that fluid momentum has no appreciable effect on drop detachment from the nozzle. The rate of flow of liquid from the supply in the syringe 9 conveniently may be regulated by a syringe pump 33 having a base 34 within which is a driving mechanism having a reciprocable driver 35 coupled to the syringe plunger 12. A suitable syringe pump is that manufactured by Harvard Apparatus (South Natick, Mass.), Model No. 22.

The optical diodes 27 and 28 are coupled by suitable wiring 36 and 37 to a source of electrical energy and to a conventional electrical pulse processor and amplifier 38 which, in turn, is electrically coupled to a timer 39, a counter 40, and a calculator 41. The signal processor and amplifier includes known analog and digital electronic circuitry. The light source 27 may be an infrared light emitting diode sold by General Electric Company under the designation LED55C, and the receiver diode 28 may comprise a photodiode sold by Motorola, Inc., under the designation MRD500. The timer and counter may be integrated and correspond to the Series 7975 controller manufactured by Veeder Root Digital Products Company.

To condition the apparatus for operation the assembly of the manifold block 1, the frame 17, and their associated parts is immersed in the liquid contained in the vessel 30. If the liquid 31 has a greater density than that of the liquid contained in the syringe 9, the drops 32 that are to be detached from the nozzle 15 will rise. Accordingly, the block 1 and the frame 17 should be oriented in the vessel 30 in the manner shown in FIG. 1. However, if the liquid 31 in the vessel 30 has a lower density than the liquid contained in the syringe 9, the block 1 and the frame 17 should be turned over from the position shown in FIG. 1 so that the drops detached from the nozzle 15 will descend.

The liquid 31 in the vessel 30 may be water or any one of a number of other liquids. The liquid in the syringe 9 may be oil or any one of a number of other liquids that essentially ar immiscible with the liquid in the vessel 30. Neither of the liquids needs to contain a surfactant, but at least one of the liquids may contain a substance that affects the interfacial tension between the two liquids. For purposes of evaluating surfactants, however, at least one of the liquids should contain a known amount of a surfactant that is chosen for its ability to reduce the liquid/liquid interfacial tension existing between the two immiscible liquids.

In use, liquid in the syringe 9 is dispensed therefrom by constant speed displacement of the piston 11 so as to deliver such liquid at a constant rate of flow to and through the bore 14 of the nozzle 15. As liquid emerges from the nozzle tip 16 it will form successive drops 32. If the liquid constituting each drop 32 has a lower density than that of the liquid 31, the drop will enlarge in size until the force of buoyancy overcomes the adherence force of the nozzle surface 16 and causes it to separate from the nozzle 15 and rise between the optical device 27 and 28 unimpeded by the cross bar 20. Such movement of the drop 32 will interrupt the beam of light transmitted from the emitter 27 to the receiver 28, thereby generating a pulse which is transmitted to the signal processor and amplifier 38 where it is amplified and transmitted to the timer 39 to energize the latter. Upon energization of the timer, the pulses generated by interruption of the light beam by successive drops 32 will actuate the counter so as to count the number of drops discharged from the nozzle. The timer can be set to be operative until a selected number of drops, such as 10, has been counted, or to remain operative for a selected time period regardless of the number of drops counted.

The precise volume of liquid discharged from the syringe easily is ascertained by automatic or manual calculations based on the displacement of the piston 11.

The interfacial tension between the two liquids can be determined from the amount of time required to form a selected number of drops at a constant flow rate. As is well known, the more effective a surfactant is in reducing interfacial tension, the smaller are the drops that will be detached from the nozzle. Thus, if one surfactant, or concentration thereof, enables the same number of drops to be formed in a lesser time period from liquid dispensed at a constant flow rate from the syringe than can be formed under the same conditions but using another surfactant or concentration thereof, the one surfactant is more effective in reducing interfacial tension.

It thus is possible to ascertain the effectiveness of a surfactant simply by comparing the time required to produce a selected number of drops from the dispensed liquid with the number of drops formed under the identical conditions, but using another surfactant or a different concentration of the same surfactant assuming, of course, that the densities of the two liquids remain relatively constant or that any change in the relative densities is known. In those instances in which automation is not required, the counting of the drops may be effected visually and the time period can be measured manually. It is preferred, however, to make use of the apparatus 38–41 for automatic timing and calculations according to Tate's law.

Rather than limiting the counting of drops to a fixed, selected number of drops, it is possible to count the number of drops that are produced at a constant flow rate in a selected period of time. In this instance the more effective surfactant will cause a greater number of drops to be formed in the same time period for the reason that the more effective surfactant will cause a greater number of drops to be produced from a given volume of dispensed liquid.

A particularly important characteristic of the invention is the use of a nozzle 15 having as small a surface area at its tip 16 as is possible. The advantage is that such a small surface area provides little area that can be wetted by either of the liquid phases and/or the components thereof, thereby providing a substantially constant circumference for drop formation at the nozzle tip. The detachment of each drop from the nozzle is dependent on the force balance between the inherent adherence force between the drop and the nozzle and the separation force. Thus when the density of the drop-forming liquid is less than that of the liquid 31, each drop will expand until its buoyancy overcomes the adherence force between the drop and the nozzle tip, and when the density of the liquid introduced into the liquid 31 is higher than that of the latter, each drop will expand until the force of gravity acting thereon exceeds the adherence force provided by the nozzle tip 16. The adherence force in each instance will be dependent on the interfacial tension between the liquids acting on the nozzle tip 16.

Because of the uniformity in size of successive drops formed by the apparatus constructed and operated in accordance with the invention, there is no necessity of utilizing Harkin's or any other correction factor in determining the interfacial tension between the two liquids. Instead, the important considerations are to ensure that the volume of liquid introduced in drop form to another liquid is known, that the number of drops counted is accurate, that the time period during which the drops are counted is known, and that the area of the nozzle outlet surface is at a minimum.

In those instances in which the method utilizes ascending drops, as is shown in FIGS. 1–4, it is desirable to avoid the accumulation of the drops at the surface of the liquid in the vessel 30. This may be accomplished by partially immersing a collector 42, such as an overturned test tube, in the path of ascending drops 32 so as to enable the latter to be collected in the test tube. The test tube may be supported by a bracket 43 secured to the frame 17.

The apparatus and methods disclosed herein provide the capability of obtaining information with respect to the dynamic characteristics of interfacial tension reduction of the liquid/liquid interface by the use of a surfactant. The disclosed methods and apparatus provide for a variable, selectable, controlled rate of growth of the interfacial area between a drop and the immiscible liquid in which the drop is accommodated. This is achieved by the appropriate selection of flow rates of liquid from the syringe over a range of 0–2 mL/Hr for most systems.

Because the rate of flow of the dispensed liquid can be varied it is possible to measure the resultant interfacial tension value between the immiscible liquids. Whenever a surfactant is present, this value is not constant because such value depends on the age of the interfacial area. For example, if the flow rate of the dispensed liquid is relatively slow, the surfactant has a greater period of time to act on the liquids at their interface. Conversely, if the flow rate is relatively fast, there is less time for the surfactant to act, so larger drops are produced. This characteristic may be used to ascertain information relating to the dynamic aspects of interfacial tension reduction.

For any particular liquid- system, the dynamic characteristic of interfacial tension reduction is unique for each different surfactant. It therefore is possible to use the dynamic data to differentiate and evaluate the performance of different surfactants or concentrations thereof. Such information can be more significant than equilibrium based interfacial tension measurements for some purposes, such as the stabilization of emulsions.

An example of dynamic analysis of one surfactant used to reduce interfacial tension between water and mineral oil is shown in FIG. 5 wherein the volume of drops is plotted against rates of flow of the mineral oil into the water. In this example the surfactant is nonionic Triton X-100, a trademark of Rohm & Haas Co., having a concentration of 5,000 ppm.

On the Y-axis is plotted the volume of a selected number of drops, obtained by the apparatus and methods hereinbefore described, and such drop volumes are proportional to interfacial tension as determined by Tate's Law. On the X-axis is plotted the rates of flow at which the mineral oil is dispensed into the water. It is possible, however, to plot on the X-axis the drop formation rate or frequency.

The reference character 44 represents an equilibrium value extrapolated to zero flow rate. The point 45 represents the average volume of 10 drops at a flow rate of 0.020 mL/Hr; the point 46 represents the average volume of 10 drops at a flow rate of 0.28 mL/Hr; and the points 47, 48, 49, and 50 represent the average volumes of 10 drops each at flow rates of 0.50, 0.75, 1.0, and 1.5 mL/Hr, respectively. The points 44–50 have been connected to form a curve 51.

The slope at any point along the curve 51 represents a measure of the resistance to change in interfacial area due to the presence of the surfactant.

Data corresponding to those shown in FIG. 5 can be obtained under identical conditions for the same liquids but using a different surfactant or a different concentration of the same surfactant. The resulting data then can be compared with one another to indicate which surfactant, or concentration thereof, is more effective in the dynamic process of interfacial tension reduction.

What is claimed is:

1. Apparatus for determining interfacial tension between immiscible liquids comprising means for containing a quantity of a first liquid; a source of supply of a second liquid immiscible with said first liquid and having a density different from that of said first liquid; delivery means in communication with and extending from said second liquid supply to an outlet capable of being immersed in said first liquid; and means for discharging via said outlet a quantity of said second liquid into said first liquid at a selected, constant rate of flow for forming successive, uniform size drops of said second liquid in said first liquid, whereby said apparatus determines said interfacial tension.

2. Apparatus according to claim 1 wherein said second liquid has a lower density than that of said first liquid.

3. Apparatus according to claim 1 wherein said second liquid has a higher density than that of said first liquid.

4. Apparatus according to claim 1 wherein said discharging means comprises a nozzle having a tip terminating in an annular wall, the thickness of said wall at said tip being less than the thickness elsewhere on the annular wall.

5. Apparatus according to claim 4 wherein the thickness of said wall at said tip approaches a razor edge.

6. Apparatus according to claim 4 wherein said tip constitutes the uppermost part of said nozzle.

7. Apparatus according to claim 4 wherein said tip constitutes the lowermost part of said nozzle.

8. Apparatus according to claim 1 including sensor means adjacent to said discharging means for sensing the presence of each successive drop.

9. Apparatus according to claim 8 including counting means coupled to said sensor means for counting each successive drop.

10. Apparatus according to claim 9 including timer means for disabling said counting means following the counting of a selected number of successive drops.

11. Apparatus according to claim 9 including timer means coupled to said counting means for limiting the operation of said counting means to a selected period of time.

12. Apparatus according to claim 8 wherein said sensor means is optical.

13. Apparatus according to claim 8 wherein said sensor means comprises a light source for emitting a light beam along a path and a receiver in said path on which said beam impinges.

14. Apparatus according to claim 13 wherein said outlet is so positioned relative to said path that each successive drop interrupts said beam.

15. Apparatus according to claim 1 including means for counting each successive drop.

16. Apparatus according to claim 1 wherein said discharging means comprises a syringe pump.

17. Apparatus according to claim 1 including means for collecting said successive drops.

18. Apparatus according to claim 1 including means for calculating the size of said drops.

19. Apparatus according to claim 1 wherein at least one of said liquids contains a surfactant.

20. Apparatus according to claim 1, wherein the rate of flow of said second liquid is maintained at a level such that the momentum of said second liquid has no appreciable effect on the formation of said drops.

21. Apparatus for determining interfacial tension between a first uniform size drop-forming liquid and a second continuous phase liquid in which said drop-forming liquid is dispensed, said first and second liquids having different densities, said apparatus comprising means for dispensing said first liquid into said second liquid at a selected, constant flow rate to form successive uniform size drops, each of said uniform size drops initially adhering to a surface portion of said dispensing means by an inherent adherence force which is proportional to the interfacial tension between the first and second liquids, whereby the drops are formed and dispensed successively into the second liquid as dictated by the force balance between the inherent adherence force and a separation force resulting from the difference in the densities between the first and second liquids; and means for calculating the size of the drops on the basis of the flow rate, the total time elapsed, and the total number of drops dispensed.

22. The apparatus of claim 21 wherein the dispensing means comprises an annular surface portion to which each drop adheres during its formation and from which it detaches into the second liquid, said surface portion having a geometry which provides a constant drop circumference for purposes of calculation of interfacial tension according to Tate's Law.

23. A method of determining interfacial tension between liquids having different densities, said method comprising introducing into a first liquid a second liquid that is immiscible with said first liquid and at a selected constant flow rate sufficient to cause said second liquid to form a plurality of successive, uniform size drops; and counting the number of said drops formed in a selected period of time.

24. The method according to claim 23 wherein the density of said first liquid is greater than that of said second liquid.

25. The method according to claim 23 wherein the density of said first liquid is less than that of said second liquid.

26. The method according to claim 23 wherein the volume of said second liquid that is introduced into said first liquid is known.

27. The method according to claim 23 wherein at least one of said first and second liquids contains a surfactant.

28. The method according to claim 27 wherein said first liquid contains said surfactant.

29. The method according to claim 27 wherein said second liquid contains said surfactant.

30. The method according to claim 27 wherein each of said first and second liquids contains said surfactant.

31. The method according to claim 23 wherein flow rate is such that the momentum of said second liquid has no appreciable effect on the formation of said drops.

32. A method of evaluating the effectiveness of a surfactant on immiscible, different density liquids at least one of which includes said surfactant, said method based upon evaluating the dynamics of interfacial tension reduction between immiscible, different density liquids in the presence of the surfactant, and said method comprising introducing into a first liquid a second liquid at a selected, constant rate of flow sufficient to cause said second liquid to form a plurality of successive, uniform size drops; and counting the number of said drops formed in a selected period of time.

33. A method of evaluating the dynamics of interfacial tension reduction between immiscible, different density liquids in the presence of a surfactant, said method comprising the steps of:
(a) discharging a second liquid into a first liquid at a selected, constant first rate of flow to produce a selected number of successive uniform size drops of said second liquid in said first liquid;
(b) discharging said second liquid into said first liquid at a selected, constant second rate of flow different from said first rate of flow to produce a number of successive uniform size drops of said second liquid in said one liquid corresponding to said selected number of drops;
(c) repeating step (b) a selected number of additional times in each of which the rate of flow is constant but different from that of the immediately preceding time; and
(d) comparing the data obtained from steps (a), (b), and (c) with corresponding data obtained from repeating steps (a), (b), and (c) using the same liquids but a different surfactant or a different concentration of the same surfactant.

34. The method according to claim 33 wherein said second rate of flow is higher than said first rate of flow and wherein the rate of flow in each of said additional time is higher than that of the immediately preceding time.

35. The method according to claim 34 including maintaining each rate of flow within a range lower than that at which the momentum of said second liquid appreciably contributes to the formation of said drops.

36. A method of determining interfacial tension between a first drop-forming liquid and a second continuous phase liquid in which said drop-forming liquid is dispensed, said first and second liquids having different densities, said method comprising the steps of dispensing said first liquid into said continuous phase at a selected, constant rate of flow to form a plurality of successive uniform size drops; counting the number of drops formed in a selected period of elapsed time; calculating the volume of the drops formed on the basis of said rate of flow, said elapsed time period, and the total number of drops formed; and calculating by Tate's Law the interfacial tension between the liquids.

* * * * *